United States Patent [19]

Ohmori et al.

[11] Patent Number: 4,581,412

[45] Date of Patent: Apr. 8, 1986

[54] COATING COMPOSITION OF VINYLIDENE FLUORIDE COPOLYMER AND ACRYLIC POLYMER

[75] Inventors: Akira Ohmori, Ibaraki; Nobuyuki Tomihashi, Takatsuki; Hiroshi Inukai; Yoshiki Shimizu, both of Settsu, all of Japan

[73] Assignee: Daikin Kogyo Co., Ltd., Osaka, Japan

[21] Appl. No.: 751,409

[22] Filed: Jul. 3, 1985

Related U.S. Application Data

[63] Continuation-in-part of Ser. No. 653,005, Sep. 21, 1984, Pat. No. 4,544,720.

[30] Foreign Application Priority Data

Sep. 21, 1983 [JP] Japan .............................. 58-175123
Mar. 6, 1985 [JP] Japan .............................. 60-44369

[51] Int. Cl.$^4$ .................. C08L 27/08; C08L 33/08; C08L 33/12
[52] U.S. Cl. .................................... 525/199; 525/200
[58] Field of Search ............................... 525/199, 200

[56] References Cited

U.S. PATENT DOCUMENTS

| | | | |
|---|---|---|---|
| 3,324,069 | 6/1967 | Koblitz et al. | 525/199 |
| 3,755,496 | 8/1973 | Koizumi et al. | 260/836 |
| 4,045,402 | 8/1977 | Bjerk et al. | 525/199 |
| 4,091,055 | 5/1978 | Kidoh et al. | 525/199 |

FOREIGN PATENT DOCUMENTS 60-21686 5/1985 Japan .

Primary Examiner—Carman J. Seccuro
Attorney, Agent, or Firm—Armstrong, Nikaido, Marmelstein & Kubovick

[57] ABSTRACT

A fluoro-resin coating composition curable at room temperature and capable of providing coatings having an improved transparency or gloss which can be maintained for a long term, as well as excellent weatherability, chemical and solvent resistances, stain resistance and adhesion to substrates, which comprises a fluorine-containing copolymer comprising vinylidene fluoride and a minor amount of a vinyl monomer having a functional group capable of causing crosslinking at room temperature in the presence of a curing agent having at least difunctionality, and an acrylic resin.

8 Claims, No Drawings

COATING COMPOSITION OF VINYLIDENE FLUORIDE COPOLYMER AND ACRYLIC POLYMER

CROSS-REFERENCE TO RELATED APPLICATION

This is a continuation-in-part of application Ser. No. 653,005 filed on Sept. 21, 1984, now U.S. Pat. No. 4,544,720.

BACKGROUND OF THE INVENTION

The present invention relates to a coating composition containing a fluorine-containing polymer, and more particularly to a room temperature curing fluoro-resin paint.

Fluoro-resin paints are excellent in chemical resistance, weatherability, stain resistance and heat resistance, but usually require baking at high temperatures. In recent years, room temperature curing fluoro-resin paints which do not require baking at high temperatures have been proposed. For instance, it is proposed to use copolymers of fluoroolefin, cyclohexyl vinyl ether and other comonomers as room temperature curing paint materials (Japanese Unexamined Patent Publication No. 55-25414, No. 57-34107 and No. 57-34108). In general, room temperature curing paints are incorporated with a lower alkyl methacrylate polymer such as polymethyl methacrylate to raise the transparency or gloss of coatings. The proposed copolymers have the defect of being poor in compatibility with the alkyl methacrylate polymer.

It is an object of the present invention to provide a room temperature curing coating composition containing a fluoro-resin which is compatible with acrylic polymers.

A further object of the invention is to provide a room temperature curing fluoro-resin coating composition which has an excellent transparency or gloss as well as weatherability, solvent resistance and the like.

These and other objects of the present invention will become apparent from the description hereinafter.

SUMMARY OF THE INVENTION

It has now been found that a particular fluorine-containing copolymer composed predominantly of 1,1-difluoroethylene (vinylidene fluoride) and having functional groups is curable at room temperature and has an excellent compatibility with alkyl acrylate or methacrylate polymers, and a composition containing the copolymer and the alkyl acrylate or methacrylate polymer provides coatings having an excellent transparency or gloss which can be kept for a long term, as well as other properties such as weatherability and chemical and solvent resistances.

In accordance with the present invention, there is provided a coating composition comprising a fluorine-containing copolymer and an acrylic resin, said fluorine-containing copolymer comprising at least 50% by mole of vinylidene fluoride and a vinyl monomer having a functional group selected from the group consisting of hydroxyl group, carboxyl group and epoxy group.

The fluorine-containing copolymer may further contain other copolymerizable monomers, especially fluoroolefins other than vinylidene fluoride.

DETAILED DESCRIPTION

The fluorine-containing copolymers used in the present invention are prepared by copolymerizing (1) vinylidene fluoride and (2) a vinyl compound having a functional group, or by copolymerizing the components (1) and (2) and (3) other copolymerizable monomers, especially fluoroolefins other than vinylidene fluoride, as the third component.

Usually, the copolymers contain (1) 50 to 99% by mole, preferably 65 to 85% by mole, of vinylidene fluoride, (2) 1 to 50% by mole, preferably 1 to 10% by mole, of the vinyl monomer having a functional group, and (3) 0 to 30% by mole, preferably 10 to 25% by mole, of a fluoroolefin other than vinylidene fluoride. When the component (3) is used, a part of the component (1) and/or the component (2) is replaced therewith. Other monomers may be further copolymerized with the above monomers so long as the physical properties of the copolymers are not substantially impaired. The copolymers having a vinylidene fluoride content of at least 50% by mole are good in chemical resistance, weatherability and stain resistance of the coating films. When the content of the vinyl compound (2) in the copolymers is from 1 to 50% by mole, the coating films obtained by reaction of the copolymers with a curing agent have good solvent resistance and flexibility, and also the copolymers dissolved in a solvent for the preparation of paints do not cause gellation even if stored for a long term and accordingly have a good storage stability. Further, the use of the fluoroolefin other than vinylidene fluoride is effective in improving the solubility in solvents of the produced copolymers.

Representative examples of the vinyl monomer (2) having a functional group are, for instance, a compound of the formula (I):

wherein X is —OH, —COOH or

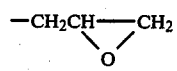

group, m is 0 or an integer of 1 to 10 and n is 0 or an integer of 1 to 4, provided that n is an integer of 1 to 4 when X is —OH group, a compound of the formula (II):

wherein X, m and n are as defined above, a compound of the formula (III):

wherein X and n are as defined above, a compound of the formula (IV):

wherein X is as defined above, Y is hydrogen atom or methyl group, and p is an integer of 1 to 4. and a compound of the formula (V):

wherein Y is as defined above.

Representative examples of the fluoroolefins other than vinylidene fluoride are, for instance, tetrafluoroethylene, chlorotrifluoroethylene, monofluoroethylene, trifluoroethylene, hexafluoropropene, and a fluoroalkyl vinyl ether such as a lower fluoroalkyl vinyl ether having a $C_1$ to $C_5$ fluoroalkyl group. Tetrafluoroethylene and chlorotrifluoroethylene are preferred.

Some of the compounds (I) are novel. The compounds of the formula: $CF_2=CF(CF_2)_m(CH_2)_nOH$ wherein m and n are as defined above, is prepared, for instance, by dechlorination or debromination of a compound of the formula:

$$CF_2X^1CFX^2(CF_2)_m(CH_2)_nOH$$

wherein $X^1$ and $X^2$ are the same or different and each is chlorine or bromine, and m and n are as defined above. The dechlorination or debromination is carried out by reacting the above compound with a dehalogenation agent such as zinc, magnesium, tin, sodium or potassium at a temperature of 0° to 150° C., preferably 50° to 100° C., at a pressure of 1 to 10 atms in a reaction solvent such as water, diemthylformamide, methanol or acetone. The compound $CF_2X^1CFX^2(CF_2)_m(CH_2)_nOH$ can be prepared by various processes for instance, by reduction of a compound of the formula: $CF_2X^1CFX^2CF_2COOR$ wherein $X^1$ and $X^2$ are as defined above and R is a lower aliphatic group or an alicyclic group, or by reduction of a compound of the formula: $CF_2X^1CFX^2(CF_2)_mCH_2CHICH_2OH$ wherein $X^1$, $X^2$ and m are as defined above and which is prepared by a radical reaction of allyl alcohol and a compound of the formula: $CF_2X^1CFX^2(CF_2)_mI$ wherein $X^1$, $X^2$ and m are as defined above.

In a like manner, the compound of the formula:

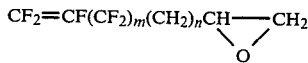

wherein m and n are as defined above, is prepared, for instance, by dechlorination or debromination of a compound of the formula:

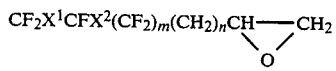

wherein $X^1$, $X^2$, m and n are as defined above. The compound of the formula: $CF_2=CF(CF_2)_m(CH_2)_nCOOH$ wherein m and n are as defined, is prepared, for instance, by dechlorination or debromination of a compound of the formula:

$$CF_2X^1CFX^2(CF_2)_m(CH_2)_nCOCl$$

wherein $X^1$, $X^2$, m and n are as defined above, followed by reaction with water. Representative examples are shown below.

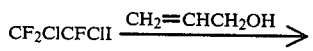 (i)

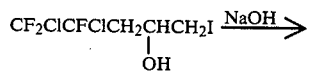

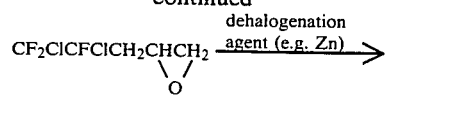

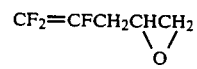

 (ii)

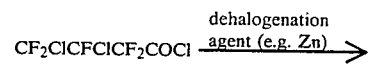

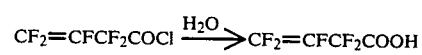

Emulsion polymerization, suspension polymerization and solution polymerization are applied to the preparation of the fluorine-containing copolymers used in the present invention. In any of the above polymerization methods, the polymerization is usually carried out at a temperature of 0° to 150° C., preferably 5° to 95° C., and at a pressure of 1 to 50 kg/cm²G.

The polymerization mediums are, for instance, water for the emulsion polymerization; water, a chlorofluorohydrocarbon such as 1,1,2-trichloro-1,2,2-trifluoroethane or 1,2-dichloro-1,1,2,2-tetrafluoroethane; and mixtures thereof for the suspension polymerization, and methyl ethyl ketone, ethyl acetate, butyl acetate and the like for the solution polymerization. In the emulsion polymerization, there are used, for instance, emulsifiers such as $C_7F_{15}COONH_4$, $H(CF_2)_8COONH_4$, $H(CF_2)_6COONH_4$, $C_7F_7COONa$ and $C_7F_{15}COONa$. Known polymerization initiators can be employed in the present invention. For instance, redox initiators consisting of as an oxidizing agent e.g. a persulfate such as ammonium persulfate or potassium persulfate, a reducing agent such as sodium sulfite, and a transition metal salt such as ferrous sulfate are employed in the emulsion polymerization. Azo compounds and organic peroxide compounds are employed in the suspension and solution polymerizations, such as azobisisobutyronitrile, isobutyryl peroxide, octanoyl peroxide and diisopropyl peroxydicarbonate.

The acrylic resins used in the present invention for preparing the coating composition include homopolymers and copolymers of alkyl acrylate or methacrylate having a $C_1$ to $C_8$ alkyl group. Examples of the acrylic resins are, for instance, homopolymers and copolymers of the alkyl acrylate or methacrylate such as methyl methacrylate, ethyl methacrylate, butyl methacrylate, cyclohexyl methacrylate or cyclohexyl acrylate; copolymers of the alkyl acrylate or methacrylate and other comonomers such as hydroxyethyl methacrylate, glycidyl methacrylate, acrylic acid, methacrylic acid, styrene and acrylonitrile: Hitaloid 3004, Hitaloid 3018 and Hitaloid 3046c which are commercially available from Hitachi Chemical Co., Ltd.; Acrydic A810-45, Acrydic A814 and Acrydic 47-540 which are commercially available from Dainippon Ink and Chemicals, Inc.; and the like. The acrylic resins used in the invention are, of course, not limited to these exemplified resins. Acrylic resins containing at least 50% by weight of methyl methacrylate and having a molecular weight of 5,000 to 300,000 (measured by gel permeation chromatography) are preferable from the viewpoint of compatibility with the fluorine-containing copolymers.

The ratio of the fluorine-containing copolymer to the acrylic resin is from 5:95 to 90:10 by weight, preferably 20:80 to 80:20 by weight. Good weatherability, transparency or gloss and pigment dispersibility are obtained within the above range.

The fluorine-containing copolymers having functional groups are curable at room temperature in the presence of a curing agent. In case of using the coating composition of the present invention as a room temperature curable paint, a compound having at least two groups capable of reacting with the functional group (hydroxyl, carboxyl or epoxy group) of the fluorine-containing copolymer to crosslink the copolymer is incorporated as a curing agent in the coating composition. The curing agent is selected according to the functional group of the copolymer. In case that the functional group is hydroxyl group isocyanates or acid anhydrides are usually employed as a curing agent. In case that the functional group is carboxyl group, isocyanates, amines, amino resins or compounds having glycidyl group are usually employed as a curing agent. In case that the functional group is epoxy group amines are usually employed as a curing agent.

Examples of the isocyanates are, for instance, hexamethylene diisocyanate, tolylene diisocyanate, hydrogenated tolylene diisocyanate, blocked diisocyanates thereof, and the like. Examples of the amines are, for instance, diethylenetriamine, triethylenetetramine, xylenediamine, m-phenylenediamine, benzyldimethylamine, bisaminopropyltetraoxa-spiro-undecane, and the like. Examples of the acid anhydrides are, for instance, phthalic anhydride, pyromellitic anhydride, trimellitic anhydride, and the like. Examples of the amino resins are, for instance, an alkyl ether of methylolmelamine, an alkyl ether of methylolurea, an alkyl ether of benzoylguanamine, and the like. Examples of the glycidyl compounds are, for instance, an aliphatic or aromatic diepoxide compound of the formula:

$$Z-R^1-Z$$

wherein Z is glycidyl group, and $R^1$ is an alkylene group having 2 to 10 carbon atoms or a bivalent aromatic group having 6 to 10 carbon atoms, an aromatic triepoxide compound of the formula:

$$Z-R^2-Z$$
$$|$$
$$Z$$

wherein $R^2$ is a trivalent aromatic group, and Z is as defined above, and the like. The curing agent used in the invention is not limited to these exemplified compounds.

The curing agent is employed in an amount of 0.5 to 2 equivalents, preferably 0.8 to 1.5 equivalents based on the functional group of the fluorine-containing copolymer.

The coating composition of the present invention is prepared by adding to the above-mentioned components, namely the fluorine-containing copolymer and acrylic resin, to a solvent, with other additives as occasion demands, in a solid concentration of 10 to 80% by weight, preferably 25 to 70% by weight, and mixing them by means of a usual mixing machine such as ball mill, paint shaker, sand mill, three roller mill or kneader.

Examples of the solvent used in preparing the coating composition are, for instance, esters such as ethyl acetate, butyl acetate, isobutyl acetate and an acetic acid ester of ethylene glycol ether; ketones such as acetone, methyl ethyl ketone and methyl isobutyl ketone; cyclic ethers such as tetrahydrofuran; amides such as dimethylformamide and N-dimethylacetamide; alcohols such as methanol, ethanol and butanol; aromatic hydrocarbons such as toluene and xylene; and the like. The solvents may be employed alone or in admixture thereof.

Additives usually employed in the preparation of coating compositions may be employed in the present invention, as occasion demands, e.g. curing accelerator, dye, pigment, viscosity controller, levelling agent, gellation inhibitor, ultraviolet absorber, antioxidant, antiskinning agent, dispersing agent, antifoaming agent, and the like.

The fluorine-containing copolymer included in the composition of the invention causes crosslinking to form a cured film for several hours to several days after applying on a substrate a mixture of a curing agent and a paint containing the copolymer, when allowed to stand at a temperature of 10° to 200° C., especially 20° to 50° C.

The room temperature curable paint composition of the present invention can be applied directly to metals such as aluminum, iron, steel, stainless steel and copper; inorganic materials such as glass, cement, concrete and ceramics; plastic materials such as polyester resin, polystyrene resin, polypropylene resin acrylic resin, vinyl chloride resin, polycarbonate resin and polyethylene resin; or organic materials such as wood and paper; or applied to one or more layers of a usual undercoat paint such as wash primer, rust inhibitive paint, epoxy resin paint, acrylic paint or polyester resin paint.

The present invention is more specifically described and explained by means of the following Examples, in which all % and parts are by weight unless otherwise noted. It is to be understood that the present invention is not limited to the Examples, and various changes and modifications may by made in the invention without departing from the spirit and scope thereof.

In order to illustrate the preparation of the fluorine-containing copolymers and acrylic resins, Reference Examples are also given below.

REFERENCE EXAMPLE 1

[Preparation of fluorine-containing copolymer]

A 1 liter autoclave was charged with 250 ml of water, 250 ml of 1,2-dichloro-1,1,2,2-tetrafluoroethane and 9.3 g of $CF_2=CFCF_2CH_2OH$ (hereinafter referred to as "M5FP"). After thoroughly replacing air in the autoclave with nitrogen gas, 24.4 g of vinylidene fluoride (hereinafter referred to as "VdF") and 2.1 g of chlorotrifluoroethylene (hereinafter referred to as "CTFE") were added to the autoclave. The autoclave was heated to 40° C. and, after thoroughly agitating the mixture, 1 g of isobutyryl peroxide was added to the autoclave to initiate the polymerization. The polymerization was carried out at 40° C. for 24 hours, while supplying a mixture of VdF, CTFE and M5FP in a ratio of 7:2:1 by mole so as to maintain the polymerization pressure at 8.5 kg/cm²G. The produced copolymer was isolated and dried at 80° C. under reduced pressure. The yield of the copolymer was 85 g.

REFERENCE EXAMPLES 2 to 9

[Preparation of fluorine-containing copolymer]

Fluorine-containing copolymers were prepared in the same manner as in Reference Example 1 except that the monomers shown in Table 1 were employed.

REFERENCE EXAMPLE 10

[Preparation of acrylic resin]

A 300 ml four necked flask was charged with 49.8 g of methyl methacrylate (MMA), 7.0 g of ethyl methacrylate (EMA) and 8.1 g of hydroxyethyl methacrylate (HEMA). After reducing the pressure, 30 g of xylene, 30 g of butyl acetate, 1.0 g of stearylmercaptan and 0.5 g of azobisisobutyronitrile were added to the flask. The mixture was heated to 70° C. with agitation, and maintained at that temperature for 7 hours. A viscous solution of an acrylic copolymer was obtained.

REFERENCE EXAMPLES 11 to 17

[Preparation of acrylic resin]

Acrylic copolymers were prepared in the same manner as in Reference Example 10 except that the monomers shown in Table 2 were employed.

REFERENCE EXAMPLE 18

A fluorine-containing copolymer to be used for comparison was prepared in the same manner as in Reference Example 1 except that the M5FP monomer was not employed.

REFERENCE EXAMPLES 19 TO 21

Acrylic copolymers to be used for comparison were prepared in the same manner as in Reference Example 10 except that the monomers shown in Table 2 were used.

TABLE 1

| Ref. Ex. No. | (Fluorine-containing copolymer) Monomer (% by mole) | | | | |
|---|---|---|---|---|---|
| | VdF | Vinyl monomer having functional group | | Fluoroolefin other than VdF | |
| | | Kind | Amount | Kind | Amount |
| 1 | 70 | M5FP | 10 | CTFE | 20 |
| 2 | 80 | M5FP | 10 | TFE | 10 |
| 3 | 70 | M5FP | 30 | — | — |
| 4 | 70 | 3FHA | 10 | CTFE | 20 |
| 5 | 70 | 7FHA | 10 | CTFE | 20 |
| 6 | 80 | M5FP | 5 | CTFE | 15 |
| 7 | 80 | HBVE | 5 | CTFE | 15 |
| 8 | 80 | 5FBA | 5 | CTFE | 15 |
| 9 | 80 | GVE | 5 | CTFE | 15 |
| 18 | 80 | — | — | CTFE | 20 |

(Notes)
M5FP: $CF_2=CFCH_2OH$
3FHA: $CF_2=CFCH_2CH_2OH$
7FHA: $CF_2=CFCF_2CF_2CH_2CH_2OH$
HBVE: $CH_2=CHOCH_2CH_2CH_2CH_2OH$
5FBA: $CF_2=CFCF_2COOH$
GVE: Glycidyl vinyl ether
CTFE: Chlorotrifluoroethylene
TFE: Tetrafluoroethylene

TABLE 2

| Ref. Ex. No. | (Acrylic resin) Monomer (% by mole) | | | | |
|---|---|---|---|---|---|
| | MMA | Vinyl monomer having functional group | | Other vinyl monomer | |
| | | Kind | Amount | Kind | Amount |
| 10 | 80 | HEMA | 10 | EMA | 10 |
| 11 | 70 | HEMA | 20 | EMA | 10 |
| 12 | 80 | HEMA | 20 | — | — |
| 13 | 65 | HEMA | 5 | EMA | 10 |
| | | | | CHMA | 20 |
| 14 | 80 | HEMA | 5 | EMA | 15 |
| 15 | 80 | HEMA | 5 | BMA | 15 |
| 16 | 80 | MA | 5 | BMA | 15 |
| 17 | 95 | GMA | 5 | — | — |
| 19 | 90 | — | — | EMA | 10 |
| 20 | 40 | HEMA | 5 | EMA | 55 |
| 21 | 40 | HEMA | 5 | BMA | 55 |

(Notes)
MMA: Methyl methacrylate
HEMA: Hydroxyethyl methacrylate
MA: Methacrylic acid
GMA: Glycidyl methacrylate
EMA: Ethyl methacrylate
CHMA: Cyclohexyl methacrylate
BMA: Butyl methacrylate

EXAMPLE 1

In a paint shaker (made by Kabushiki Kaisha Toyo Seiki Seisakusho), 20 g of a 50% methyl ethyl ketone solution of the fluorine-containing copolymer obtained in Reference Example 1, 20 g of a 50% toluene solution of the acrylic resin obtained in Reference Example 10, 6 g of rutile titanium dioxide, 10 g of toluene and 0.005 g of dibutyl tin laurate were mixed for 2 hours. To 20 g of the obtained mixture was added 4.5 g of hexamethylene diisocyanate trimer (commercially available under the trade mark "Colonate EH" made by Nippon Polyurethane Kabushiki Kaisha) to give a room temperature curing paint.

The obtained paint was applied to an aluminum plate (BT-712 treatment, made by Nippon Test Panel Co., Ltd.) coated with an undercoat paint ("Hipon 20 Ace" made by Nippon Paint Co., Ltd., film thickness 45 μm) by spraying, and allowed to stand at room temperature for 7 days. The obtained film had a thickness of 25 μm and a good gloss. The following tests were made by using the aluminum plate with the above paint film as a specimen.

The results are shown in Table 3.

Pencil hardness

The hardness was measured according to Japanese Industrial Standard (JIS) K 5400.

Adhesion

The paint film was cross-cut by a knife into 100 squares each having a size of 1×1 mm, and a cellophane adhesive tape was repeatedly stuck and peeled off 10 times. The number of remaining squares was counted.

Gloss

The 60° specular gloss was measured according to JIS K 5400.

Weatherability

The exposure test was conducted for 4,000 hours under conditions of 18 min./120 min. in rain shower cycle, 60% in humidity and 63° C. in black panel temperature by using a Sunshine Weather-O-Meter (made by Suga Shikenki Kabushiki Kaisha). The gloss retention rate was obtained from the glosses before and after exposure.

Solvent resistance

A tissue paper ("Kimwipe" made by Jujo Kimberly Kabushiki Kaisha) was impregnated with methyl ethyl ketone, and the paint film was rubbed with the paper 20 times. The gloss was measured and the solvent resistance was estimated according to the following criteria.
◉ : No change in gloss
○ : 1-3 point decrease in gloss
△ : 5-10 point decrease in gloss
● : 20 or more point decrease in gloss.

EXAMPLES 2 to 12

The procedures of Example 1 were repeated except that the fluorine-containing copolymers and acrylic resins shown in Table 3 were employed.
The results are shown in Table 3.

COMPARATIVE EXAMPLES 1 to 5

The procedures of Example 1 were repeated except that the fluorine-containing copolymers and acrylic resins shown in Table 4 were employed.
The results are shown in Table 4.

COMPARATIVE EXAMPLE 6

The procedure of Example 1 was repeated except that a copolymer of chlorotrifluoroethylene, hydroxybutyl vinyl ether cyclohexyl vinyl ether and n-butyl vinyl ether in a molar ratio of 50:10:20:20 was employed instead of the fluorine-containing copolymer obtained in Reference Exampel 1.
The pencil hardness, adhesion, solvent resistance and gloss were 2H, 100, and 32, respectively. and accordingly the gloss was very bad.

amount of acrylic resins is too small or too large, improvement in gloss or gloss rentention is bad, and that the use of acrylic resins containing at least 50% by weight of methyl methacrylate is preferable in improving the gloss of the paint films.

In addition to the ingredients used in the Examples, other ingredients can be used in the Examples as set forth in the specification to obtain substantially the same results.

What we claim is:
1. A coating composition comprising a fluorine-containing copolymer and an acrylic resin, said fluorine-containing copolymer comprising at least 50% by mole of vinylidene fluoride, and a vinyl monomer having a functional group selected from the group consisting of hydroxyl group carboxyl group and epoxy group.
2. The composition of claim 1, wherein said copolymer comprises 50 to 99% by mole of vinylidene fluoride and 1 to 50% by mole of said vinyl monomer having a functional group.
3. The composition of claim 1, wherein said copolymer comprises 50 to 99% by mole of vinylidene fluoride 1 to 50% by mole of said vinyl monomer having a functional group and at most 30% by mole of a fluoroolefin other than vinylidene fluoride.
4. The composition of claim 3, wherein said fluoroolefin is tetrafluoroethylene or chlorotrifluoro-ethylene.
5. The composition of claim 1, wherein said acrylic resin is an alkyl acrylate or methacrylate polymer.
6. The composition of claim 1, wherein said fluorine-containing copolymer and said acrylic resin are present in a ratio of 5:95 to 90:10 by weight.
7. The composition of claim 1, wherein said fluorine-containing copolymer and said acrylic resin are present in a ratio of 20:80 to 80:20 by weight.

TABLE 3

| Ex. No. | Fluorine-containing copolymer Kind | part | Acrylic resin Kind | part | Pencil hardness | Adhesion | Solvent resistance | Gloss | Gloss retention |
|---|---|---|---|---|---|---|---|---|---|
| 1 | Ref. Ex. 1 | 50 | Ref. Ex. 10 | 50 | H | 100 | ◉ | 81 | 93 |
| 2 | Ref. Ex. 2 | 70 | Ref. Ex. 11 | 30 | H | " | " | 73 | 95 |
| 3 | Ref. Ex. 3 | 50 | Ref. Ex. 12 | 50 | 2H | " | " | 78 | 91 |
| 4 | Ref. Ex. 4 | 70 | Ref. Ex. 10 | 30 | HB | " | " | 71 | 93 |
| 5 | Ref. Ex. 5 | 50 | Ref. Ex. 11 | 50 | H | " | " | 80 | 91 |
| 6 | Ref. Ex. 6 | 70 | Ref. Ex. 13 | 30 | H | " | " | 75 | 96 |
| 7 | Ref. Ex. 7 | 70 | Ref. Ex. 14 | 30 | HB | " | " | 76 | 95 |
| 8 | Ref. Ex. 6 | 50 | Ref. Ex. 15 | 50 | H | " | " | 80 | 95 |
| 9 | Ref. Ex. 6 | 80 | Ref. Ex. 14 | 20 | HB | " | " | 73 | 94 |
| 10 | Ref. Ex. 6 | 20 | Ref. Ex. 14 | 80 | 2H | " | " | 85 | 85 |
| 11 | Ref. Ex. 8 | 50 | Ref. Ex. 16 | 50 | 2H | " | " | 81 | 92 |
| 12 | Ref. Ex. 9 | 50 | Ref. Ex. 17 | 50 | 2H | " | " | 79 | 93 |

TABLE 4

| Com. Ex. No. | Fluorine-containing copolymer Kind | part | Acrylic resin Kind | part | Pencil hardness | Adhesion | Solvent resistance | Gloss | Gloss retention |
|---|---|---|---|---|---|---|---|---|---|
| 1 | Ref. Ex. 18 | 50 | Ref. Ex. 19 | 50 | H | 65 | ● | 78 | 35 |
| 2 | Ref. Ex. 6 | 95 | Ref. Ex. 14 | 5 | 2B | 100 | ○ | 55 | 85 |
| 3 | Ref. Ex. 6 | 2 | Ref. Ex. 14 | 98 | 3H | 100 | ○ | 85 | 20 |
| 4 | Ref. Ex. 6 | 50 | Ref. Ex. 20 | 50 | HB | 95 | ○ | 20 | — |
| 5 | Ref. Ex. 6 | 50 | Ref. Ex. 21 | 50 | B | 97 | ○ | 20 | — |

It is observed in Table 3 that the coating composition of the present invention has excellent gloss, weatherability, solvent resistance, adhesion to substrates and hardness. Also, it is observed in Table 4 that when the 8. The composition of claim 1, wherein said acrylic resin contains at least 50% by weight of methyl methacrylate.

* * * * *